United States Patent [19]

Schmitz

[11] Patent Number: 5,301,846
[45] Date of Patent: Apr. 12, 1994

[54] SPRAY BOTTLE

[75] Inventor: Detlef Schmitz, Lunen, Fed. Rep. of Germany

[73] Assignee: Perfect-Valois Ventil GmbH, Dortmund, Fed. Rep. of Germany

[21] Appl. No.: 779,872

[22] Filed: Oct. 21, 1991

[30] Foreign Application Priority Data

Mar. 1, 1991 [DE] Fed. Rep. of Germany ....... 4106575

[51] Int. Cl.$^5$ .................. B65D 37/00; B65D 1/32
[52] U.S. Cl. .................. 222/211; 239/327; 222/481.5
[58] Field of Search .......... 239/327, 418, 433; 222/211, 206, 481.5

[56] References Cited

U.S. PATENT DOCUMENTS

| 2,564,000 | 8/1951 | Hall | 239/327 |
| 2,642,313 | 6/1953 | Montenier | 239/327 |
| 2,700,484 | 1/1955 | Rathsprecher | 222/211 |
| 3,176,883 | 4/1965 | Davis, Jr. | 222/193 |
| 3,361,304 | 1/1968 | Thompson | 239/327 |
| 3,381,860 | 5/1968 | Armour | 239/327 |
| 3,622,049 | 11/1971 | Thompson | 239/327 |
| 4,286,735 | 9/1981 | Sneider | 239/327 |
| 5,110,051 | 5/1992 | Bennett | 222/211 |

FOREIGN PATENT DOCUMENTS 1491707 7/1973 Fed. Rep. of Germany .
607738 9/1960 Italy .................. 239/327
679400 12/1962 Italy .................. 239/327

Primary Examiner—Andres Kashnikow
Assistant Examiner—Christopher G. Trainor
Attorney, Agent, or Firm—Dressler, Goldsmith, Shore & Milnamow, Ltd.

[57] ABSTRACT

The invention relates to a flexible spray bottle (10) for nasal spray, onto the bottle neck (14) of which a spray cap (12) is placed. The top wall (17) of the spray cap (12) contains a spray opening (20) and, on the underside, a connection piece (18) for a dip tube (21). A mixing-air passage (30, 31) extends between the connection piece (18) and the dip tube (21), with the result that a liquid-/air mixture leaves the spray opening (20). An annular flange (15) of the spray cap (12) contains an air-admitting passage (23) which extends radially in the flange and is angled inside the spray cap towards the interior of the bottle (10). The angled part contains an air-admitting valve with a valve body (28) which is pressed against a valve seat (27) in the case of positive pressure in the container and seals off the air-admitting passage (23). In the open position of the air-admitting valve, the valve body (28) rests on supporting arms (29) which make possible the passage of air through the air-admitting passage (23). The spray bottle prevents bodily secretions from being sucked up after the introduction of the medicament into the nasal passage and while retaining customary design features makes possible economical production (FIG. 1).

1 Claim, 1 Drawing Sheet

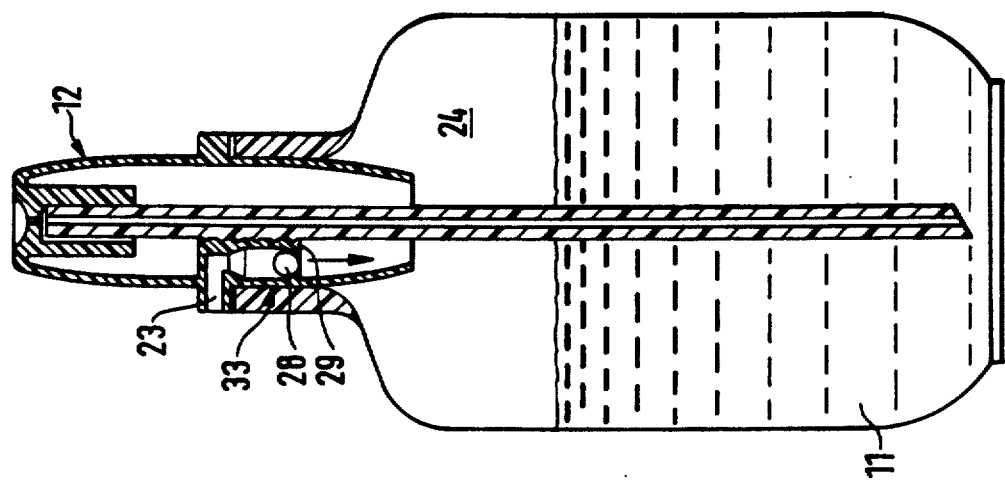
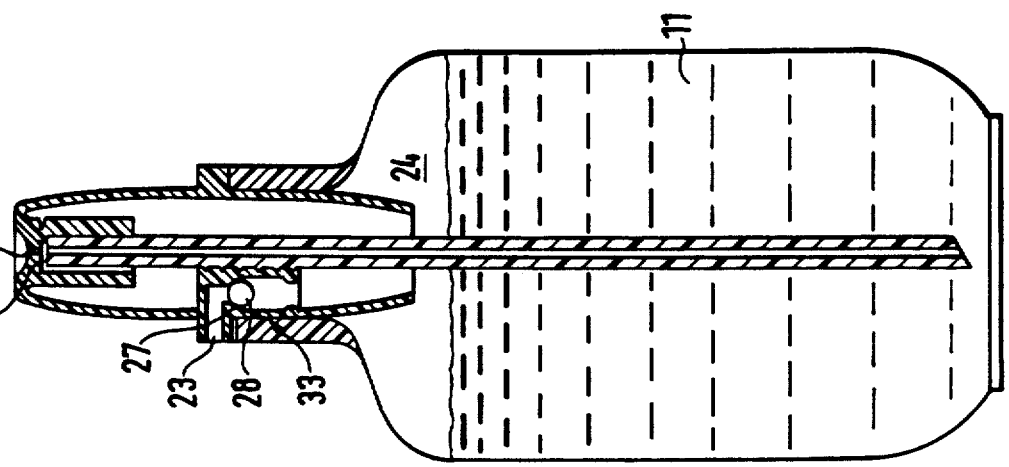
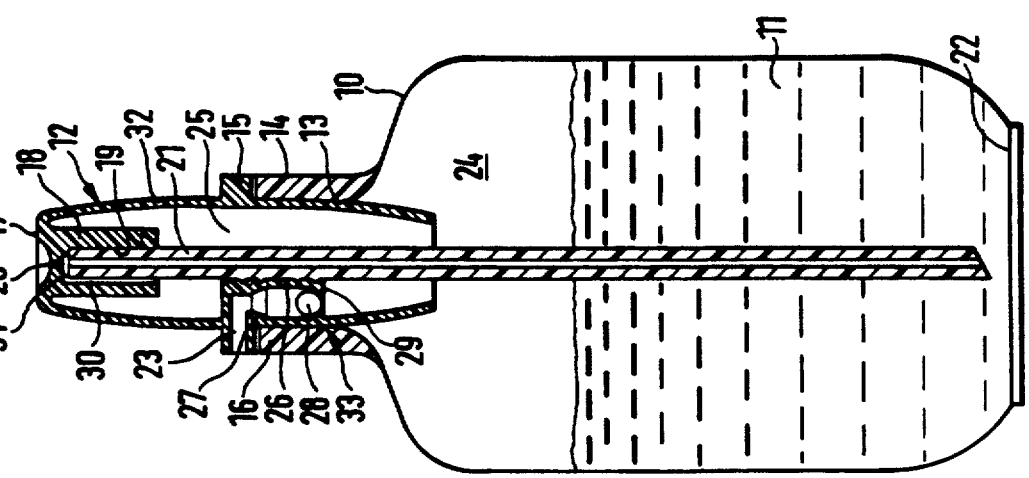

SPRAY BOTTLE

The invention relates to a flexible spray bottle which can be compressed by hand, having the features contained in the preamble of patent claim 1.

A spray bottle of this generic type is disclosed in U.S. Pat. No. 3,176,883. The spraying device of this known spray bottle is exceptionally complicated even if it is ensured that no nasal secretion is sucked up when air is admitted to the spray bottle after the forcing out of the medicoment into the nasal passage.

It is the underlying object of the invention, while largely retaining the construction of known nasalspray bottles made of plastic, to make possible a facility for the admission of air to the bottle which is simple in structure but acts rapidly without the possibility of secretions from the body cavity being sucked up through the spray opening. At the same time, economical production should be guaranteed.

The invention solves this object by virtue of the fact that the air-admitting passage extends in the annular flange of the spray cap, radially to the major axis of the latter, into the annular space between the inner cap wall and the dip tube and, in the annular space, is angled towards the interior of the spray bottle, the upper end of the angled passage portion being provided with a valve seat and the lower end of the passage portion being provided with a holding device for a valve body of the air-admitting valve, said device making possible the admission of air to the interior of the spray bottle.

The invention is explained in greater detail below by means of the schematic drawing of an illustrative embodiment of a spray bottle. In the drawing:

FIG. 1 shows a central longitudinal section through a spray bottle in the rest position;

FIG. 2 shows the spray bottle according to FIG. 1 in the actuation position and

FIG. 3 shows the spray bottle according to FIG. 1 or 2 in the suction position.

The figures show a flexible spray bottle 10 which can be compressed by hand, is made of plastic and is intended for the introduction of a preferably liquid medicoment 11 into an orifice, preferably a nasal passage, of a human or animal body. A spray cap 12 is inserted sealingly with an approximately cylindrical plug 13, which tapers slightly towards the bottom, into a neck 14 of the spray bottle 10, said neck forming the bottle opening. The spray cap 12 rests by an outer annular flange 15 on the upper end rim 16 of the bottle neck 14. An elastic cap wall 32 having a diameter matched to the body orifice extends upwards from the annular flange 15 with a taper similar to that of a truncated cone and forms a top wall 17. A cylindrical connection piece 18 with a recess 19 projects downwards from the underside of the top wall, which is provided with a spray opening 20. The spray opening 20 is arranged coaxially to the recess 19. Inserted into the recess 19 is a dip tube 21 which extends as far as the bottom 22 of the bottle and is connected to the spray opening 20. Also provided is an air-admitting passage 23 for the air space 24 inside the spray bottle 10, said air-admitting passage 23 being allocated a shut-off valve 33 which is closed only in the case of positive pressure in the spray bottle.

The air-admitting passage 23 extends in the annular flange 15 of the spray cap 12, radially to the major axis of the latter, into the annular space 25 between the inside of the cap wall 32 and the dip tube 21 and as far as the dip tube. In the region of the annular space 25, the air-admitting passage 23 is angled downwards towards the interior of the container and is here bounded by the inside of the approximately cylindrical plug 13 of the spray cap at the outside and by a wall 26 which extends in parallel along the dip tube 21. The upper end of the downward-angled air-admitting passage 23 is provided with a valve seat 27 for a valve body 28. In the illustrative embodiment under consideration, the valve body 28 comprises a ball. This valve ball can be made of metal. The surface of the ball can be covered with a layer of plastic if there is a risk of unfavorable chemical reactions between the active substance contained in the bottle and the metal. In this case, the valve ball may also be produced completely from plastic. However, other shapes for the valve body are also conceivable e.g. a flexible plastic tongue.

The lower end of the downward-angled portion of the air-admitting passage 23 is provided with a holding device for the valve body 28, said holding device permitting the admission of air to the interior 24 of the spray bottle 10. This holding device comprises supporting arms which project radially inwards into the free cross-section of the air-admitting passage, are arranged distributed with circumferential spacing relative to one another and leave a cross-section free between them even when the valve body 28 is resting on these supporting arms. As d result, air is admitted to the interior 24 of the spray bottle 10 in FIG. 1 since the outside air is continuously connected to the interior 24 via the air-admitting passage 23 and the cross-sections of passage left free by the valve body 28 in the open position and via the annular space 25 between the plug 30 and the dip tube 21.

A mixing-air passage 30 extends between the connection piece 18 and the dip tube 21 as far as a mixing space 31, which is arranged between the outlet of the dip tube 21 and the spray opening 20 and serves to mix the liquid 11 contained in the bottle with the air and in this way to achieve a fine division of the spraying liquid in the spray jet which leaves the spray opening 20.

In the actuated condition of the spray bottle in FIG. 2, the product is sucked up through the dip tube by the free atmosphere due to the positive pressure brought about by the compression of the flexible walls of the bottle and is mixed in advance in the mixing space 31 with the air compressed in the interior 24. As is evident, the compressed air in the interior 24 of the spray bottle presses the valve ball 28 onto its upper valve seat, preventing the air contained in the container from escaping to the outside through the air-admitting passage.

As soon as the flexible walls of the bottle return to their starting position again after their actuation, the valve body is moved back into its lower air-admitting position according to FIG. 3, with the result that the outside air can ventilate the interior 24 of the bottle rapidly via the air-admitting passage 23 and past the valve body in the position shown in FIG. 3 and, produce a pressure compensation by virtue of which the walls of the bottle can rapidly reassume their original position and the spray bottle is ready for the next spraying operation.

It is evident that the simple construction of the spray cap and of the air-admitting valve arranged therein requires only slight changes to known spray caps and thus makes possible effective air admission to a spray bottle of this kind, which is preferred for nasal spray, without bodily secretions being sucked up into the bottle through the spray opening during the admission of air to the spray bottle.

What is claimed is:

1. A flexible plastic spray bottle having a neck rim, which bottle can be compressed by hand and is intended for the introduction of a liquid medicament into a body orifice, and an approximately cylindrically shaped spray cap having a plastic cap wall adapted to be inserted into an opening defined by the neck rim, said spray cap resting on the rim of the bottle neck and including an outer annular flange from which the plastic cap wall tapers upwards in the manner of a truncated cone with the diameter matched to the body orifice and forms a top wall from the underside of which there projects a cylindrical connection piece with a recess, said connection piece defines a spray opening arranged coaxially to the recess, a dip tube is disposed in said recess and one end extends to the bottom of the bottle and its other end is located adjacent said spray opening, the inside of the plastic cap wall and the dip tube defines an annular space, said spray cap also defines an air admitting passage in which is located a shut-off valve means that is closed only in response to positive pressure in the spray bottle, the air admitting passage is located in said annular flange of the spray cap and is generally of an inverted L shape including a radially extending portion connecting up with a downwardly extending portion that extends toward the interior of the spray bottle, said downwardly extending portion defines at its upper end a valve seat for a spherical valve member disposed therein which seats on the valve seat when the bottle is squeezed to exhaust said medicament from the spray bottle and the cap defines at the lower end of the downwardly extending portion a holding device for the valve member, the holding device permits the admission of air past the valve member to the spray bottle when a partial vacuum exists in the spray bottle when the bottle is released, said holding device at the lower end of the downwardly extending portion of the air-admitting passage comprises support arms for the valve member that define air flow passages open even when the spherical valve member is resting on the support arms.

* * * * *